United States Patent [19]

Kennedy

[11] 4,011,616
[45] Mar. 15, 1977

[54] TEETH CLEANING DEVICE
[76] Inventor: Carroll W. Kennedy, 696 Neff Road, Grosse Pointe, Mich. 48230
[22] Filed: May 14, 1975
[21] Appl. No.: 577,291
[52] U.S. Cl. .............................. 15/21 R; 128/62 A
[51] Int. Cl.² ......................................... A46B 13/02
[58] Field of Search ............... 15/22 R, 22 A, 22 C, 15/167 A, 21 R; 128/62 A, 65, 67

[56] References Cited
UNITED STATES PATENTS

| | | | |
|---|---|---|---|
| 1,818,146 | 8/1931 | Maker | 15/167 A X |
| 2,319,205 | 5/1943 | Buck | 15/22 R |
| 3,769,652 | 11/1973 | Rainer | 15/167 A |
| 3,874,084 | 4/1975 | Cole | 128/62 A |

Primary Examiner—Edward L. Roberts
Attorney, Agent, or Firm—Harness, Dickey & Pierce

[57] ABSTRACT

A vibrating toothbrush comprising a soft shoe bristled on one side and having a metal structural skeleton. The shoe is capable of being formed over a human dental arch so that the bristles will be in contact with the teeth. The shoe can be detachably connected to a horseshoe-shaped base which in turn is connected to a vibrating apparatus.

9 Claims, 14 Drawing Figures

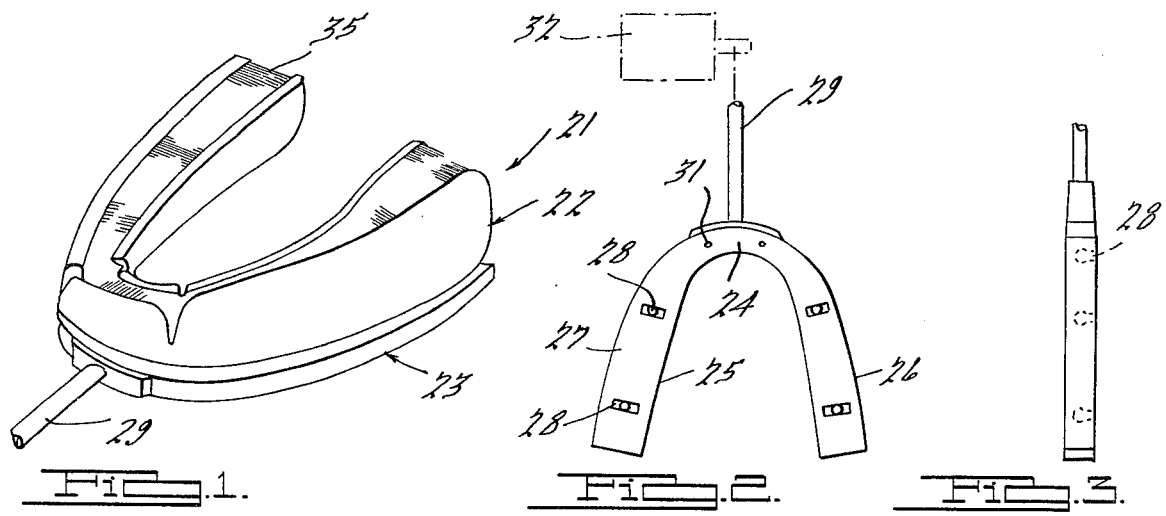
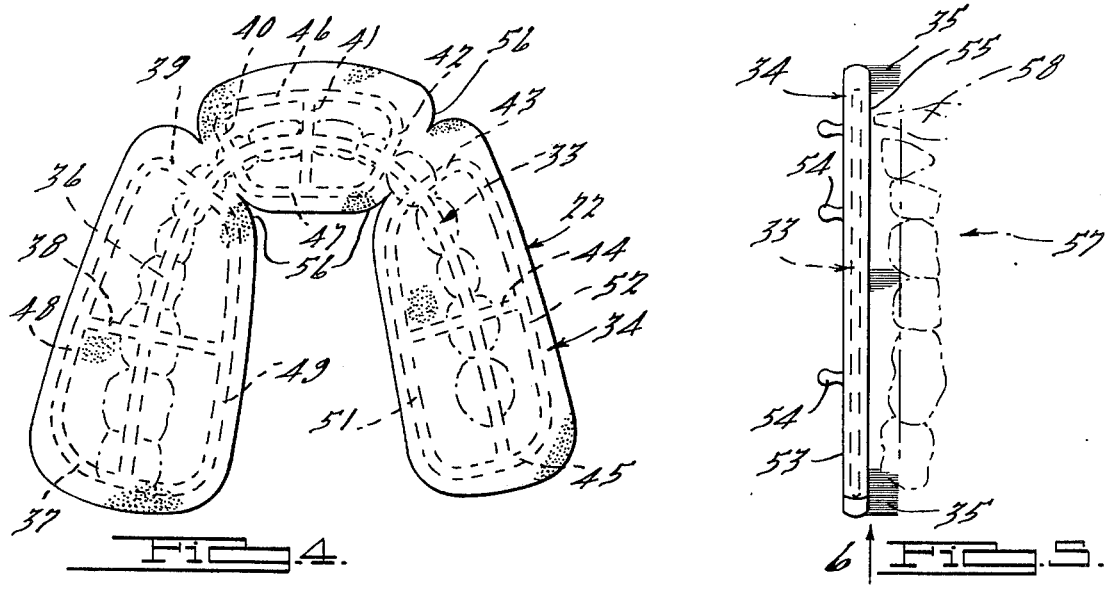
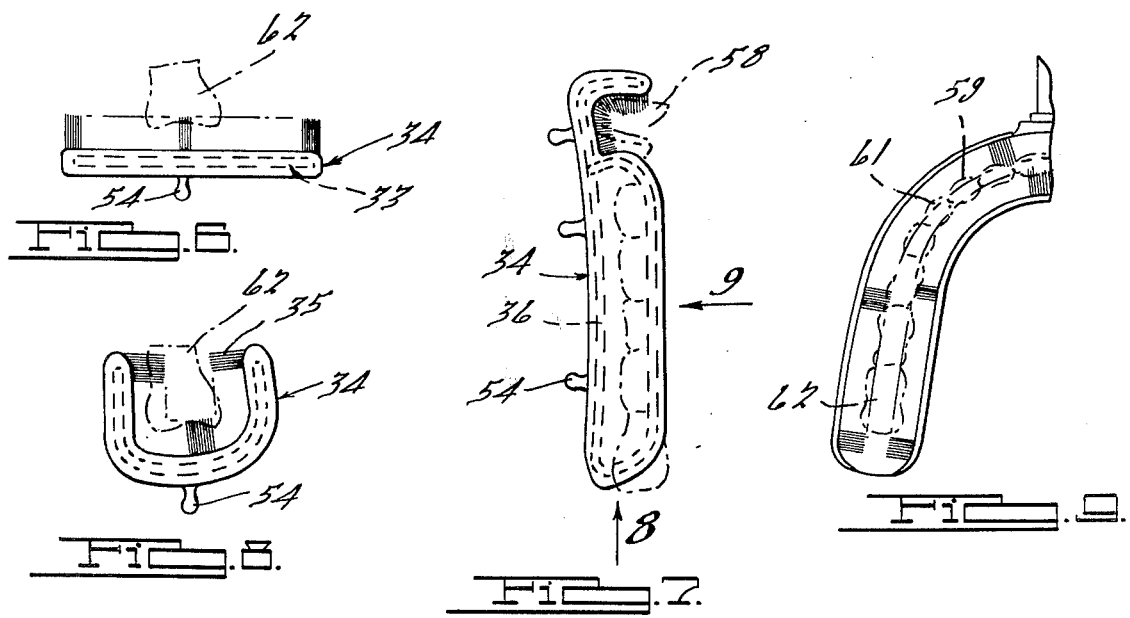

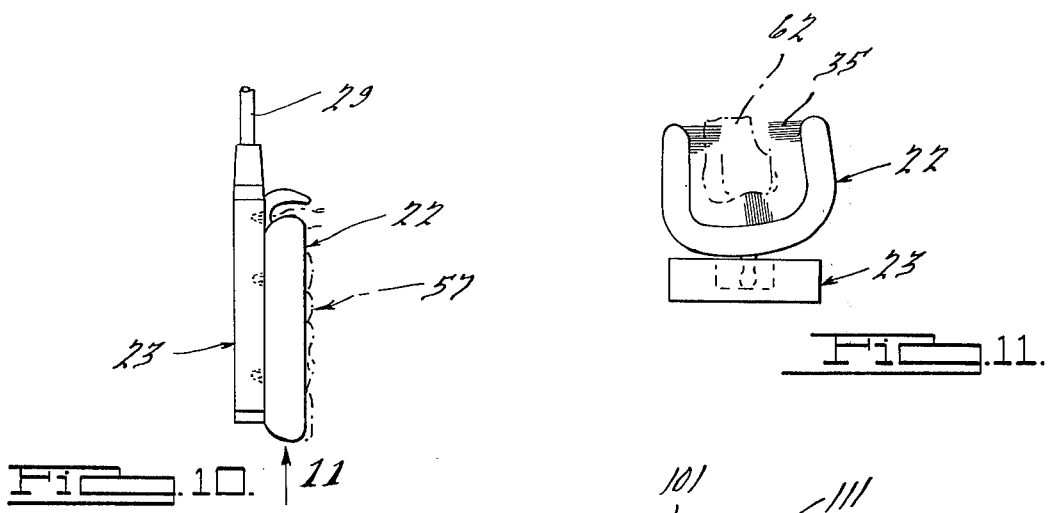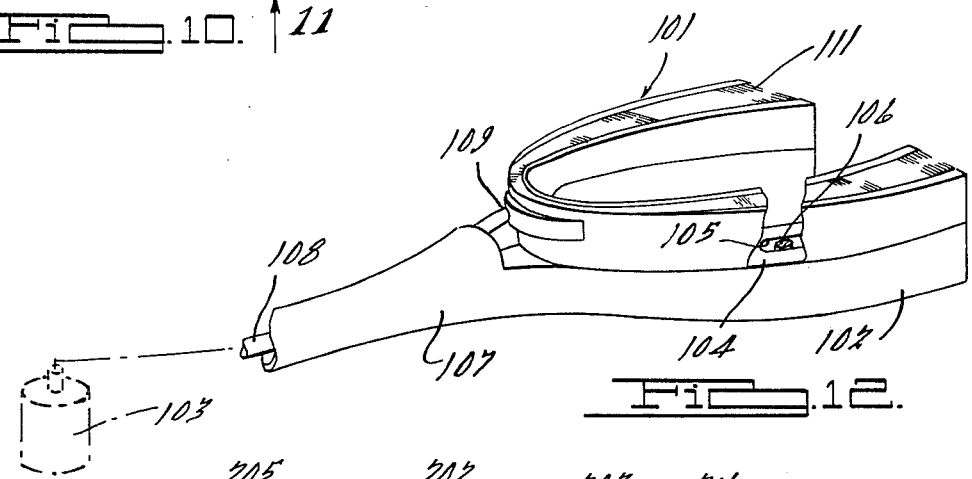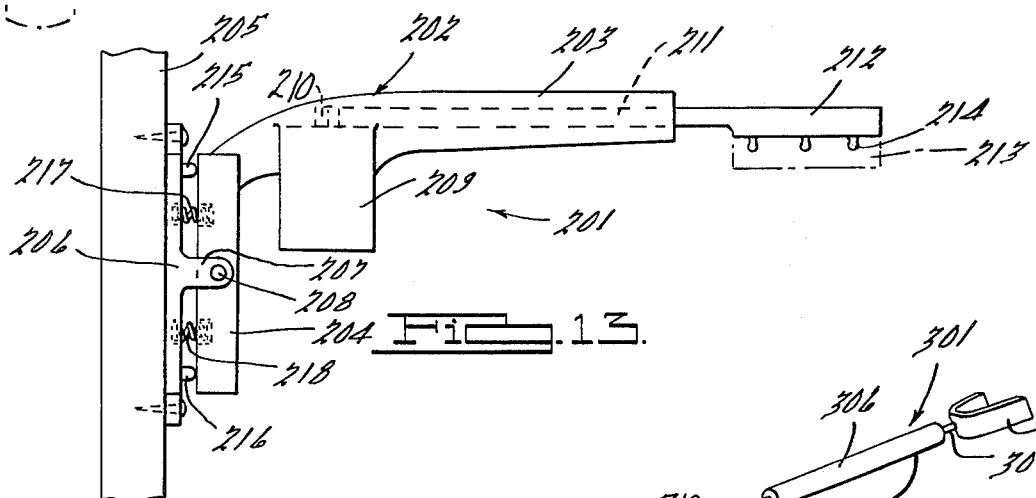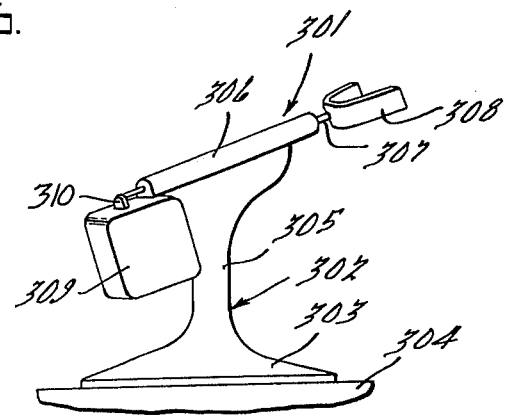

TEETH CLEANING DEVICE

BACKGROUND OF THE INVENTION

1. Field of the Invention

The invention relates to dental cleaning devices, and more particularly to vibrating toothbrushes and toothbrushes of the type having channel-shaped members of horseshoe configuration and inwardly extending bristles.

2. Description of the Prior Art

Vibrating toothbrushes of conventional straight configuration are well known, and Maker U.S. Pat. No. 1,818,146 shows a horseshoe-shaped gum massaging device connectable to a vibrator. Rainer U.S. Pat. No. 3,769,652 discloses a chewing toothbrush with upper and lower horseshoe-shaped channels of resilient material and inwardly extending bristles. Bauer U.S. Pat. No. 3,163,874 shows another type of horseshoe-shaped toothbrush in which the bristles are supported by wire. Other patents developed in a search on the subject of this invention are U.S. Pat. No. 1,668,385 to Szekely, Reissue No. 23,975 to Keely, U.S. Pat. No. 3,065,479 to McGee, U.S. Pat. No. 3,230,572 to Leonard, and U.S. Pat. No. 3,335,443 to Parisi et al.

These prior devices have certain shortcomings as compared with the present invention, which will become apparent from the following description.

BRIEF SUMMARY OF THE INVENTION

It is an object of the present invention to provide a novel and improved horseshoe-shaped toothbrush which is easily adjustable to individual dental configurations in which there may be peculiarities such as missing teeth or teeth out of alignment, and which will hold the adjusted shape while still cleaning the teeth in a firm but gentle manner.

It is another object to provide an improved toothbrush of this nature which is capable of being formed over the human dental arch and once formed can be detachably connected to a horseshoe-shaped base which in turn is connected to a vibrating apparatus.

It is also an object to provide a toothbrush having these characteristics, which is capable of cleaning tooth surfaces, interdental spaces, and specific gum tissue surfaces by a quivering or pulsating type of vibration, loosening plaque formation and at the same time maintaining and stimulating healthy blood circulation to the gum surfaces.

It is a further object to provide an improved vibrating toothbrush of this character which is especially useful for persons presently unable to brush their own teeth, such as victims of a disabling disease or injury. In conjunction with this object, it is a purpose of the invention to reduce the cost of institutional dental health programs by minimizing the need for hospital personnel assigned to manually brush teeth of incapacitated persons, and reducing the number of vibrating units for a large number of patients.

It is another object to provide an interchangeable vibrating toothbrush which makes a proper dental health home care program available to families.

Briefly, the toothbrush of this invention comprises a horseshoe-shaped skeleton fabricated of a ductile metal, said skeleton having a central portion along its extent and lateral portions extending on both sides thereof, a covering surrounding said skeleton, said covering being fabricated of a soft flexible material, and bristles embedded in one side of said covering, whereby the lateral portions of said skeleton along with said covering and bristles may be bent out of the plane of said central portion to form a channel shape, and all portions of said skeleton, covering and bristles may be formed to fit an individual dental arch.

In another aspect, the invention comprises a toothbrush having a horseshoe configuration and channel-shaped cross section, the brush being fabricated of soft material with embedded bristles on one side, a base detachably supporting said brush, and a vibrator connected to said brush.

The invention also comprises a toothbrush of horseshoe configuration and channel-shaped cross section having a soft cover with embedded bristles on one side, a vibrator connected to said brush, bracket means supporting said vibrator and brush on a stationary object whereby a person unable to hold the brush may place one set of teeth in the channel-shaped brush, and means permitting the brush to be reversed while still connected to said vibrator whereby the other set of teeth may be placed therein.

BRIEF DESCRIPTION OF THE DRAWINGS

FIG. 1 is a perspective view of a first embodiment of the invention with the toothbrush shown in its formed position;

FIG. 2 is a top plan view of the base before attachment of the brush;

FIG. 3 is a side elevational view of the base;

FIG. 4 is a top plan view of the brush before the sides have been formed to fit a dental arch;

FIG. 5 is a side view of the brush showing the manner in which it overlaps the teeth and the attaching means for the base;

FIG. 6 is an end elevational view, taken in the direction of the arrow 6 of FIG. 5, of one portion of the brush before the sides are bent to fit the dental arch;

FIG. 7 is a view similar to FIG. 5 but with sides bent to fit the teeth;

FIG. 8 is an end view in the direction of the arrow 8 of FIG. 7 showing one portion of the brush;

FIG. 9 is a partial plan view taken in the direction of arrow 9 of FIG. 7;

FIG. 10 is a side view of the brush attached to the base;

FIG. 11 is an end elevational view taken in the direction of the arrow 11 of FIG. 10;

FIG. 12 is a perspective view of another embodiment of the invention in which the vibrator is connected directly to the brush which is movably mounted on the base;

FIG. 13 is a view of still another embodiment of the invention in which the toothbrush is supported by a wall-mounted bracket; and FIG. 14 is a side view of yet another embodiment of the invention in which the vibrating mechanism and brush are supported by a table bracket.

DESCRIPTION OF THE PREFERRED EMBODIMENTS

Referring first to the embodiments of FIGS. 1–11, the appliance is generally indicated at 21 in FIG. 1 and comprises a brush generally indicated at 22 and a base generally indicated at 23. The base is of flat horseshoe shape as seen in FIGS. 2 and 3, having a central portion 24 with legs 25 and 26 extending therefrom. The shape of base 23 approximates the curvature of a dental arch, with the central portion 24 being somewhat narrower than legs 25 and 26. Base 23 may be fabricated of a hard plastic or similar rigid material, and has a flat brush supporting surface 27. A plurality of slotted clip sockets 28 are formed in surface 27 of legs 25 and 26 to detachably receive clips on the brush which are described below. A rod 29 is secured by fasteners 31 to the outside of central portion 24 of the base and leads to a vibrating mechanism. This mechanism may be of any conventional type and is shown schematically by the dot-dash rectangle 32 in FIG. 2.

The construction of brush 22 is seen best in FIGS. 4 through 9. Like base 23, the brush is of generally horseshoe configuration and has a skeleton generally indicated at 33, a body or covering generally indicated at 34, and bristles 35. Skeleton 33 is illustrated as being fabricated of wire which is of considerable strength relative to body 34 but is nevertheless ductile and formable.

Although the skeleton is shown as being fabricated of wire elements, it could also be fabricated of one or more stampings or in other ways consistent with the principles of the invention.

The skeleton has a central portion along its extent in the form of a spine 36 having an arched horseshoe shape, and a plurality of transverse ribs 37 through 45. Ribs 40, 41 and 42 extend in opposite directions from the midsection of spine 36 and are connected at their outer ends by wires 46 and 47 which have curved junctures with end ribs 40 and 42. Similarly, ribs 37, 38 and 39 extend from one side section or leg of spine 36 and are connected by wires 48 and 49, while ribs 43, 44 and 45 extending from the other leg of the spine are united at their outer ends by wires 51 and 52. The result is that skeleton 33 is made up of a plurality of independently bendable sections which can be curved upwardly from spine 36 to fit an individual dental arch, with the spine itself being also bendable in any direction to accommodate the shape of the arch.

Skeleton 33 is completely embedded in and surrounded by covering 34. The covering is fabricated of a soft moldable plastic or similar substance which will not harm gum tissue, will adapt to arch, teeth and gum margins, receive and transmit vibrations to the bristles 35 and be strong enough to retain them. Like skeleton 33, covering 34 will be flat in its initial state as seen in FIG. 5. The undersurface 53 of covering 34 is provided with attaching clips 54 receivable by sockets 28 of base 23. The opposite surface 55 of covering 34 has embedded in it bristles 35. The bristles preferably cover the entire surface 55 of the cover and are of sufficient strength to furnish the desired cleansing and vibrating action, yet pliable enough to be molded and shaped around the teeth.

Preferably, a plurality of recesses 56 are formed in the edges of covering 34 between the central portion and the sides thereof as seen in FIG. 4. These recesses, located between the sets of skeleton ribs, facilitate the upward bending and shaping of those portions of covering 34 which surround the independently movable portions of skeleton 33 described above.

FIGS. 5 and 6 show brush 22 in its original flat shape before being formed to fit a particular dental arch. The arch is indicated generally in dot-dash lines at 57 and comprises incisors 58, canines 59, bicuspids 61 and molars 62. It should be understood that the dental arch configuration shown in the drawings is merely typical and that some subjects could have missing or misaligned teeth.

FIGS. 5 through 9 show how brush 22 is shaped to fit a particular dental arch. It will be seen that the skeleton and covering, together with the bristles, are bent upwardly section by section and adjusted to properly accommodate the arch, with the spine 36 likewise being bent to fit. The skeleton will hold the covering and bristles firmly in their adjusted position. After the fitting has been accomplished, brush 22 may be mounted on base 23 as shown in FIGS. 10 and 11. The assembly is then ready to be used.

In operation, the user will place either his upper or lower teeth in brush 22 and turn on the vibrating mechanism. Rod 29 will have a very slight reciprocating, quivering or pulsating action which will be transmitted through skeleton 33 and covering 34 to bristles 35 to clean the tooth surfaces, interdental spaces and specific gum tissues by vibration, loosening plaque formation and stimulating blood circulation in the gum tissues.

After the upper teeth have been cleaned, the user need merely invert the assembly and place the other set of teeth in brush 22 to clean them in the same manner as previously.

Since brush 22 is removable, the same base 23 and vibrating mechanism 32 may be used with a number of interchangeable and possibly differently colored brushes, all of them having the same location of clips 54. In this manner, a hospital or other institution, for example, need provide only a limited number of vibrating mechanisms and bases for a large number of patients, each patient having his or her individual brush 22.

FIG. 12 shows a second embodiment of the invention which is basically similar to the first but in which the brush, generally indicated at 101, is movably mounted on base 102, the vibrating mechanism 103 being connected directly to brush 101 instead of to the base. Base 102 is of horseshoe shape with its upper surface 104 provided with a plurality of brush retaining slots 105. Brush 101 has downwardly extending clips 106 detachably mounted in slots 105, the arrangement being such that slight movement at least in a longitudinal or back-and-forth direction, and preferably in multiple directions, is permitted between the brush and base. Base 102 has a tubular extension 107 within which extends a flexible rod or cable 108, one end of this rod being connected at 109 to the central portion of brush 101. The other end of rod 108 is connected to the vibratory mechanism. As in the previous embodiments, brush 101 may comprise a skeleton, soft surrounding body or covering and bristles 111 embedded in the body and facing the channel shaped tooth receiving groove after the body has been properly formed. A detachable connection may be provided at the juncture 109 between cable 108 and the central portion of the brush so that the brush may be properly fitted.

In operation of the embodiment of FIG. 12, the reciprocating movement of cable 108 will cause brush 101 to vibrate on base 102 to clean one set of teeth. After completion, the assembly comprising the base and brush may be inverted to be in position for cleaning the other set.

FIG. 13 shows a third embodiment of the invention similar to the previous embodiment and especially adapted for use by patients or others who are unable to hold a tooth cleaning mechanism while brushing their teeth. The device is generally indicated at 201 and comprises a bracket generally indicated at 202 having a horizontal portion 203 and a vertical portion 204. The vertical portion is mounted on a wall or other support 205 by a member 206 having a base attached to the wall and an extension 207 to which bracket portion 204 is pivoted at 208. A vibrating mechanism 209 is mounted on bracket 202 and has a horizontally reciprocating extension 210 connected to an extension 211 of a base 212. Extension 211 is guided by bracket portion 203 and is so mounted that base 212 may be inverted in order that the brush shown in dot-dash lines at 213, and mounted on clips 214 of base 212, may be inverted to brush either the upper or lower teeth of the patient.

A pair of switches 215 and 216 are provided for controlling operation of the vibrating mechanism 209 in accordance with the patient's wishes. These switches have plungers engageable with the upper and lower ends respectively of vertical portion 204 of bracket 202, above and below pivot 208. A pair of springs 217 and 218 normally hold bracket 202 in a centered position so that no operative pressure is applied to either switch plunger 215 or 216. Counterclockwise swinging of the bracket from its FIG. 13 position will close switch 215 to actuate the vibrating mechanism 209 when the patient desires to brush his lower teeth. Similarly, after inverting brush 213, the patient may press down to swing bracket 202 clockwise and close switch 216, operating the vibrating mechanism while he brushes his upper teeth.

FIG. 14 shows another embodiment of the invention which is similar to those previously described but in which the device is intended to be supported on a table such as a bedside stand. The unit is generally indicated at 301 and comprises a stand generally indicated at 302 having a base 303 which rests on table 304. Stand 302 has a column 305 supporting an inclined tube 306. This tube guides a shaft 307 on the upper end of which a brush 308 is mounted. The brush may be constructed as those of the previous embodiments. The lower end of rod 307 is connected to a vibrating mechanism 309 carried by stand 302 and having a reciprocating extension 310. Switches (not shown) may be conveniently located as in FIG. 13 for the patient so that after he has placed either his upper or lower teeth in brush 308, he may operate vibrating mechanism 309.

What is claimed:

1. A toothbrush having a horseshoe configuration and channel-shaped cross section, the brush being fabricated of soft material with embedded bristles on one side, a base detachably supporting said brush, a vibrator connected to said brush through said base, and a wall-mounted bracket supporting said vibrator and said brush, said base and brush being invertible whereby upper and lower teeth may be sequentially cleansed.

2. The combination according to claim 1, further provided with switch means responsive to upward pressure on said brush for operating said vibrator when the brush is on the lower teeth, switch means responsive to downward pressure on said brush to operate the vibrator when the brush is on the upper teeth, and means preventing operation of the vibrator when there is neither downward or upward pressure.

3. The combination according to claim 2, said last-mentioned means comprising a pivotal mounting for said bracket, and spring means holding the bracket in a neutral position, said switch means being on opposite sides of the pivotal mounting.

4. A toothbrush having a horseshoe configuration and channel-shaped cross section, the brush being fabricated of soft material with embedded bristles on one side, a base detachably supporting said brush, a vibrating mechanism connected directly to said brush, and interconnecting means between the brush and base permitting limited motion of the brush with respect to the base at least in a longitudinal direction.

5. A toothbrush having a horseshoe configuration and channel-shaped cross section, the brush being fabricated of soft material with embedded bristles on one side, a base detachably supporting said brush, a vibrator connected to said brush, a stand supporting said vibrator, a shaft interconnecting said vibrator and brush, and a guide tube for said shaft supported by said stand.

6. A toothbrush having a horseshoe configuration and channel-shaped cross section, the brush comprising a skeleton formed of relatively strong but ductile metal, a covering surrounding said skeleton formed of a material soft enough not to harm gum tissue, and bristles retained on one side of said covering, the covering having flat upper and lower surfaces in its original condition but being bendable along with said bristles and skeleton to fit a particular dental arch and tooth configuration, a base detachably supporting said brush, and a vibrator connected to said brush.

7. A dental cleaning device comprising a brush of horseshoe configuration and channel-shaped cross section, said brush comprising a metal skeleton, a soft covering in which said skeleton is embedded, and bristles on one side of said covering, the covering being of material which is sufficiently soft to not harm gum tissue whereby the covering, bristles and skeleton may be formed to fit a dental arch and tooth configuration, a base of horseshoe configuration having a brush supporting surface, interconnecting means on the brush and base for detachably mounting the brush on the base, means stationarily supporting the base, means permitting the brush and base to be inverted whereby both upper and lower teeth may be cleansed, a vibrating mechanism connected to said brush, and means for operating said vibrating mechanism.

8. A dental cleaning device comprising a base having a flat surface, a brush having a body and bristles, a flat surface on said body engageable with said base surface, interfitting clip-and-socket means on said two surfaces for detachably retaining said body on said base, said clip-and-socket means comprising a plurality of spaced sockets on said base, and a plurality of clips extending from said body and receivable by said sockets, and means secured to and extending from said base for moving the base in a vibratory manner.

9. A dental cleaning device comprising a base having a flat surface, a brush having a body and bristles, a flat surface on said body engageable with said base surface, interfitting clip-and-socket means on said two surfaces for detachably retaining said body on said base, said clip-and-socket means comprising a plurality of spaced sockets on said base, and a plurality of clips extending from said body and receivable by said sockets, the sockets being enlarged so as to permit relative movement between the base and body, means secured to and extending from said body for causing vibrating motion thereof in at least one direction, and means on said base for supporting the entire assembly.

* * * * *